United States Patent [19]
Schlossman et al.

[11] Patent Number: 5,843,635
[45] Date of Patent: Dec. 1, 1998

[54] INHIBITION OF APC-MEDIATED APOPTOSIS OF ACTIVATED T LYMPHOCYTES

[75] Inventors: Stuart F. Schlossman, Newton; Mei X. Wu, Cambridge, both of Mass.

[73] Assignee: Dana-Farber Cancer Institute, Inc., Boston, Mass.

[21] Appl. No.: 395,149

[22] Filed: Feb. 27, 1995

[51] Int. Cl.[6] .......................... C12Q 1/70; G01N 33/564; C07K 16/00
[52] U.S. Cl. ................................ 435/5; 436/506; 530/387
[58] Field of Search .................................. 530/387; 435/5; 436/506

[56] References Cited

PUBLICATIONS

Banda et al., "Crosslinking CD4 by Human Immunodeficiency Virus gp120 Primes T Cells for Activation–induced Apoptosis," *J. Exp. Med*, 176:1099–1106 (1992).
Debatin et al., "High Expression of APO–1 (CD95) on T Lymphocytes From Human Immunodeficiency Virus–1–Infected Children," *Blood* 83:3101–3103 (1994).
Embretson et al., "Massive covert infection of helper T lymphocytes and macrophages by HIV during the incubation period of AIDS," *Nature* 362:359–362 (1993).
Finkel et al., "Apoptosis occurs predominantly in bystander cells and not in productivity infected cells of HIV–and SIV–infected lymph nodes," *Nature Medicine* 1:129–134 (1995).
Giorgi et al., "T–Cell Subset Alterations in HIV–Infected Homosexual Men: NIAID Multicenter AIDS Cohort Study," *Clinical Immunology and Immunopathology* 52:10–18 (1989).
Gougeon et al., "Programmed Cell Death in AIDS–Related HIV and SIV Infections," *Aids Research and Human Retroviruses* 9:553–563 (1993).
Groux et al., "Activation–induced Death by Apoptosis in CD4[+] T Cells from Human Immunodeficiency Virus–infected Asymptomatic Individuals," *J. Exp. Med.* 175:331–340 (1992).
Kabelitz et al., "Life and death of a superantigen–reactive human CD4[+]0 T cell clone: staphylococcal entertoxins induce death by apoptosis but simultaneously trigger a proliferative response in the presence of HLADR+ antigen–presenting cells," *International Immunolgy* 4:1381–1388 (1992).
Kabelitz et al., "Activation–induced cell deth (apoptosis) of mature peripheral T lymphocytes," *Immunology Today* 14:338–339 (1993).
Kizaki et al., "Activation of a Suicide Process of Thymocytes Through DNA Fragmentation By Calcium Ionophores and Phorbol Esters," *The Journal of Immunology* 143:1790–1794 (1989).

(List continued on next page.)

*Primary Examiner*—Ponnathapura Achutamurthy
*Assistant Examiner*—Hankyel T. Park
*Attorney, Agent, or Firm*—Weingarten, Schurgin, Gagnebin & Hayes LLP

[57] ABSTRACT

Methods for interfering with antigen presenting cell-mediated priming of resting peripheral blood T lymphocytes to undergo activation induced cell death ("apoptosis") by inhibiting an interaction between a membrane associated molecule ("an APC apoptotic ligand") present on stimulated antigen presenting cells ("APC") and a counter-receptor that is present on T lymphocytes are disclosed. The antigen presenting cells are preferably from the monocyte/macrophage cell line or are dendritic cells. Also disclosed are methods of screening for inhibitors of APC-mediated priming of T lymphocytes to undergo apoptosis and methods and agents for detecting, identifying and characterizing an APC apoptotic ligand. Inhibitors identified by the screening method of the invention are used to reduce the T lymphocyte depletion associated with HIV infection and thereby mitigate the severe immunodeficiency associated with AIDS by interfering with the association between HIV-infected antigen presenting cells, especially monocytes and macrophages, and T cells.

8 Claims, 5 Drawing Sheets

PUBLICATIONS

Meyaard et al., "Programmed Death of T Cells in HIV–1 Infection," *Science* 257:217–219 (1992).

Meyaard et al., "Programmed Death of T Cells in Human Immunodeficiency Virus Infection," *J. Clin. Invest.* 93:982–988 (1994).

Mosier et al., Macrophage–tropic HIV: critical for AIDS pathogeneis? (1994).

Mosier et al., "Rapid Loss of CD4$^+$ T Cells in Human–P-BL–SCID Mice by Noncytopathic HIV Isolates," *Science* 260:689–692 (1993).

Nieto et al., "IL–2 Protects Against Anti–CD3–Induced Cell Death In Human Medullary Thymocytes," *The Journal of Immunology* 1451364–1368 (1990).

Razvi et al., "Programmed Cell Death of T Lymphocytes during Acute Viral Infection: a Mechanism for Virus–Induced Immuno Deficiency," *Journal of Virology* 67:5754–5765 (1993).

Schmid et al., "Sensitive Method for Measuring Apotosis and Cell Surface Phenotype in Human Thymocytes by Flow Cytometry," *Cytometry* 15:12–20 (1994).

Schuitemaker et al., "Lack of T–Cell Dysfuntion and Programmed Cell Death in Human Immunodeficiency Virus Type–1–Infected Chimpanzees Correlates with Absence of Monocytotropic Variants,".

Smith et al., "Antibodies to CD3/T–cell receptor complex induce death by apotosis in immature T cells in thymic cultures," *Nature* 337:181–184 (1989).

Uehara et al., "Apoptotic Cell Death of Primed CD45RO$^+$ T Lymphocytes in Epstein–Barr Virus–Induced Infectious Mononucleosis," *Blood* 80:452–458 (1992).

Veis et al., "Expression of the Bcl–2 Protein in Murine and Human Thymocytes and in Peripheral T Lymphocytes," *The Journal Of Immunology* 151:2546–2554 (1993).

Wesselborg et al., "Induction of Activation–Driven Death (Apoptosis) in Activated but Not Resting Peripheral Blood T Cells," *The Journal of Immunology* 150:4338–4345 (1993).

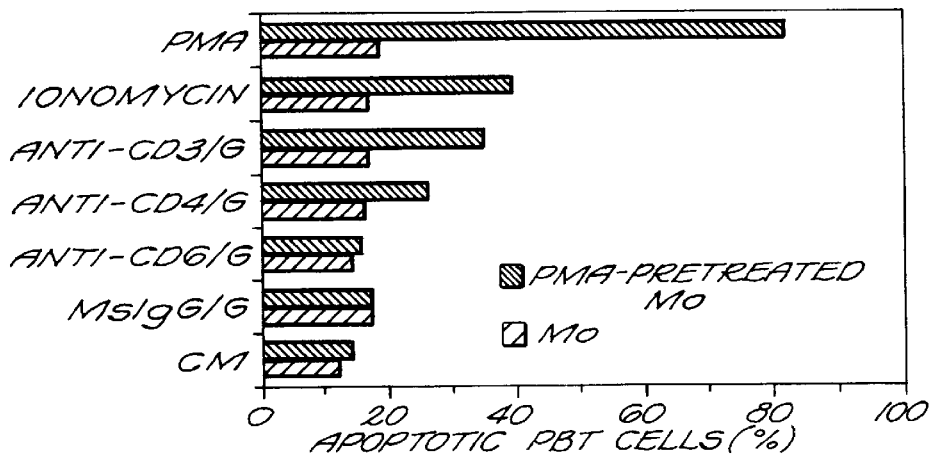
FIG. 3
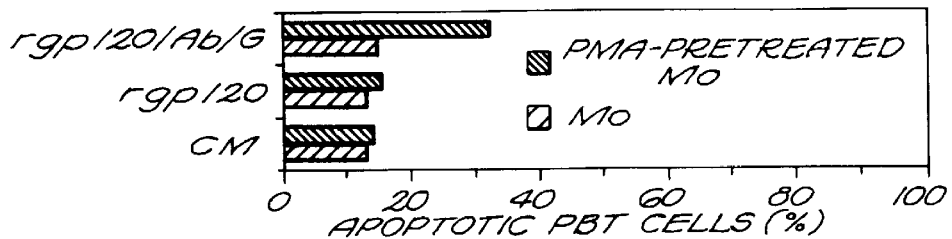
FIG. 5A
FIG. 5B

INHIBITION OF APC-MEDIATED APOPTOSIS OF ACTIVATED T LYMPHOCYTES

GOVERNMENT RIGHTS

Research leading to this invention was supported in part by Grant Nos. AI 2069 and CA34283 from the National Institutes of Health of the United States. Therefore, the U.S. Government has certain rights in this invention.

FIELD OF THE INVENTION

This invention relates to the prevention of activation induced cell death in peripheral blood T lymphocytes.

BACKGROUND

Lymphocytes become activated when antigen receptors on the cell surface are cross-linked, or when they are exposed to agents that mimic this signal. Although such activation is usually associated with the production of immune mediators (e.g. antibodies, cytokines) and entry into the cell cycle, it can alternatively lead to programmed cell death or apoptosis. Treatment with anti-CD3 antibody, ionomycin, and/or phorbol ester can induce apoptosis in both human and mouse immature thymocytes (Smith et al., Nature 337:181–184 1989; Nieto et al., J. Immunol. 145:1364–1368 1990). However, truly resting mature T cells are resistant to the induction of apoptosis (Kizaki et al., J. Immunol. 143:1790–1794 1989; Wesselborg et al., J. Immunol. 150:4338–4345 1993) and it is believed that this resistance to apoptosis may be correlated with T cell maturity. Bcl-2, a known proto-oncogene that can block apoptosis, is present at much higher levels in mature, peripheral T cells than in immature thymocytes (Veis et al., J. Immunol., 151:2546–2554 1993) and within the mouse thymus, mature $CD3^{bright}$ thymocytes are largely resistant to apoptosis induced by glucocorticoid treatment compared with immature $CD3^{-/dim}$ thymocytes (Scmid et al., Cytometry 15:12–20 1994). Such findings have suggested that upregulation of CD3 expression in thymocytes correlates with cell survival and selection for export into the periphery.

Peripheral blood T (PBT) cells can gradually acquire susceptibility to apoptosis induced by anti-CD3 mAb, antigen and mitogenic activation, or by cytokine-induced cycling after extended culture (Wesselborg et al., J. Immunol., 150:4338–4345 1993). Apoptosis can be induced as well in T lymphoblasts, transformed T cells, and T-cell hybridomas by treatment with anti-CD3 antibody and susceptibility to apoptosis has also been demonstrated with some long-lived T cell clones (Kabelitz et al., Int. Immunol., 4:1381–1388 1992). In these cases, it is thought that this acquired susceptibility to apoptosis by mature T cells may be linked to the Fas (CD95)-dependent death pathway (Kabelitz et al., Immunol. Today, 4:1381–1388 1992). These findings suggest that the PCD pathway may be absent or inactivated during the differentiation of T lymphocytes yet may reappear following prolonged stimulation.

In contrast to PBT cells isolated from healthy individuals, a significant number of PBT cells isolated from HIV-infected individuals die through apoptosis upon overnight culture in vitro (Meyaard et al., Science 257:217–219 1992). This apoptosis of T cells occurs in both $CD4^+$ and $CD8^+$ cell populations and is enhanced by activation in vitro with anti-CD3, ionomycin, PWM, or SEB, i.e., with reagents which stimulate normal PBT cells to proliferate (Groux et al., J. Exp. Med. 175:331–340 1992; Gougeon et al., AIDS Research & Human Retroviruses 9:553–563 1993). PBT cells from HIV infected individuals do express low levels of both activation (Giorgi et al., Clin. Immunol. and Immunopathol. 52:10–18 1989) and CD95 (Fas/Apo-1) antigens (Debortin et al., Blood 83:3101–3103 1994) and they are apparently non-dividing cells. Nevertheless, it is still not clear why PBT cells in HIV-infected individuals are so susceptible to apoptosis triggered by T cell stimulation. Determining the answers to such a question may be crucial in understanding the mechanisms underlying the decline in the number of $CD4^+$ lymphocytes which occurs with disease progression in AIDS patients.

SUMMARY

The invention is based upon the novel observation that phorbol myristate acetate (PMA)-activated monocytes (Mo) can prime peripheral blood cells to undergo activation-induced apoptosis. This result appears to be the first demonstration that resting peripheral blood T cells can be readily induced to undergo apoptosis by stimulating via cross-linking of CD3 or CD4 molecules, ionmycin or PMA through a non-MHC-restricted monocyte-dependent mechanism. In accordance with our discovery, it will be possible to reduce the T lymphocyte depletion associated with HIV infection, and thereby mitigate the severe immunodeficiency associated with AIDS, by interfering with the association between HIV-infected antigen presenting cells, especially monocytes and macrophages, and T cells.

We have shown that a membrane associated molecule or ligand is expressed on the monocyte cell surface early after activation with PMA and that close contact between this ligand (or ligands) and T cells is required for induction of apoptosis. Inhibitors that block the activity of the ligand at the level of receptor binding, such as blocking antibodies, soluble receptor, receptor antagonists and small molecules, should be useful in inhibiting macrophage induced apoptosis of $CD4^+$ and $CD8^+$ T cells.

Therefore, in general the invention features methods for interfering with APC-mediated priming of T lymphocytes to undergo activation induced cell death ("apoptosis") by inhibiting an interaction between a membrane associated molecule ("an APC apoptotic ligand") present on stimulated antigen presenting cells ("APC") selected from a group consisting of monocytes, macrophages and dendritic cells (especially follicular dendritic cells, lymphoid dendritic cells, and Langerhans cells) and a counter-receptor that is present on T lymphocytes, by exposing the APC apoptotic ligand or the T cell counter-receptor to an inhibitor or general antagonist. The term "antagonist" as used here includes any agent that interacts with the indicated molecule and interferes with its function. The antigen presenting cell is preferably a monocyte or macrophage. The inhibition can take place extracellularly, with the inhibitor being, for example, polyclonal anti-sera, a monoclonal antibody, fragment, or derivative that binds to an epitope that is present on the APC apoptotic ligand, a soluble receptor based upon the structure of an apoptotic ligand, a peptide or small molecule drug, or any agent that prevents adhesion between the antigen presenting cell and the T lymphocyte.

In an alternative embodiment, the inhibition could occur intracellularly, by inhibiting normal expression of an APC apoptotic ligand. This might involve inhibition of complex formation or anti-sense approaches, approaches that would inhibit transcription factor binding to the promoter of an APC apoptotic ligand gene or intracellular immunization approaches in which the inhibition involves the intracellular expression of an anti-APC apoptotic ligand. In intracellular inhibition, a preferred anti-APC apoptotic ligand would be a single chain antibody that is expressed by a suitable expression vector in vivo.

The invention is also directed to a novel APC apoptotic ligand isolated from PMA-stimulated monocytes, which is not present on PMA-stimulated B lymphocytes and which can prime peripheral blood T lymphocytes to undergo activation driven cell death. The ligand can be isolated from solubilized cell lysates from PMA-stimulated human monocytes or it can be produced by recombinant genetic engineering techniques. Soluble forms of a novel APC apoptotic ligand are also within the scope of the invention. The invention further includes an isolated nucleic acid encoding an APC apoptotic ligand, antibodies to the APC apoptotic ligand, and fragments and derivatives of the APC apoptotic ligand, including the ligand or fragment thereof as part of a fusion protein, e.g., as an IgG fusion protein.

In another aspect, the invention is directed to methods of screening for inhibitors of APC-mediated priming of T lymphocytes to undergo activation induced cell death. Such methods include conducting an apoptosis assay with and without candidate inhibitors, and detecting inhibition as measured by any standard apoptosis detection method, e.g., cell staining, visualization of DNA fragmentation by electrophoretic separation of DNA, visualization of nuclear collapse using microscopy (electron or light), cell staining, FACS and propidium iodide staining. Such screening methods can be in vitro or in vivo. An in vivo screen would use the SCID hu mouse model as disclosed in Mosier et al., Science 260:689–692 (1993). The relative number of cells in control samples versus samples to which candidate inhibitors have been added can be determined by FACS analysis. The antigen presenting cells used in in vitro screens are preferably either PMA activated macrophages or monocytes or APCs infected with a macrophage-trophic strain of HIV (e.g., HIV-1 SF162, HIV-2UCI). Many other macrophage-trophic strains of HIV-1 and HIV-2 are known and could alternatively be used.

The invention also features therapeutic methods for inhibiting T cell depletion associated with lentivirus infection (HIV, SIV), or infection with other viral diseases associated with lymphocyte depletion, such as cytomegalovirus (CMV), Epstein Barr virus (EBV) and LCMV. The methods for moderating activation induced cell death in T lymphocytes in a mammal involve inhibiting the interaction between a membrane-associated molecule that is present on stimulated mammalian monocytes macrophages or dendritic cells but not present on the corresponding unstimulated cell ("APC apoptotic ligand"), and a counter-receptor that is present on mammalian T lymphocytes, by exposing the APC apoptotic ligand or the T cell counter-receptor to an inhibitor. The inhibitor can be of any of the previously mentioned types. In preferred aspects of the therapeutic method, the mammal is a human being, a SCID hu mouse repopulated with human peripheral blood lymphocytes, or a macaque monkey infected with a lentivirus. Based upon what is known at present about T cell depletion in HIV-infected patients, we believe that treatments of this type could be most useful where the patient is in an asymptomatic phase of HIV infection and T cell counts have begun to fall. Given that T cell depletion continues after the onset of AIDS, the therapeutic approaches of the invention might also be useful in the acute phase of HIV infection. Treatments according to the methods of the invention can be used in combination with other approaches.

BRIEF DESCRIPTION OF THE DRAWINGS

The file of this patent contains at least one color photograph. Copies of this patent with color photograph(s) will be provided by the Patent and Trademark Office upon request and payment of the necessary fee.

The invention will be more fully understood from the following detailed description taken in conjunction with the accompanying drawings in which:

FIG. 3 shows the results of an experiment to determine if contact or close proximity between PBT cells and Mo is required for the induction of apoptosis of PBT cells;

FIGS. 5A and 5B show the effect of T cell stimulation in inducing apoptosis of PBT cells cultured with PMA-pretreated Mo.

DETAILED DESCRIPTION OF THE INVENTION

Although freshly-isolated, human peripheral blood T (PBT) cells are largely resistant to the apoptotic effects of anti-CD3 mAb, ionomycin, or phorbol myristate acetate (PMA), we have unexpectedly discovered that PBT cells, including both $CD4^+$ and $CD8^+$ cell populations, can be readily induced to undergo apoptosis when cocultured with either autologous or allogeneic monocytes (Mo) in PMA-containing medium. Phytohaemagglutinin (PHA) has a similar ability to prime resting PBT cells for apoptosis.

In brief, incubation of PBT cells with Mo at a ratio of 1:1 for 18 hr was shown to result in maximal levels (80%) of apoptotic cell death. As will be described in more detail below, the mechanism whereby Mo enable PBT cells to undergo apoptosis in PMA-containing medium appears to depend upon cell-cell contact or close-proximity between Mo and PBT cells rather than solely via soluble mediators. We have demonstrated that Mo acquire the ability to prime PBT cells for apoptosis after treatment with PMA, and that treated Mo maintain this ability even after fixation with formaldehyde. We have also found that once PBT cells became primed for apoptosis by incubation with PMA-pretreated Mo, the primed PBT cells were susceptible to apoptosis triggered not only by PMA but also by either ionomycin or by mAb crosslinking of T cell surface molecules such as CD4 and CD3. Interestingly, the degree of apoptosis of $CD4^+$ T cells by crosslinking of CD4 molecules via a combination of gp120, anti-gp120 and goat anti-mouse IgG was significantly greater for T cells primed with PMA-treated Mo than for unprimed T cells. Together, these findings reveal an important role for accessory cells in priming resting PBT cells for apoptosis and suggest a Mo-dependent mechanism by which T cells may become primed for apoptosis in HIV-infected asymptomatic individuals.

PBT Cells Undergo Apoptosis in the Presence of Both Mo and PMA

Figure 1:
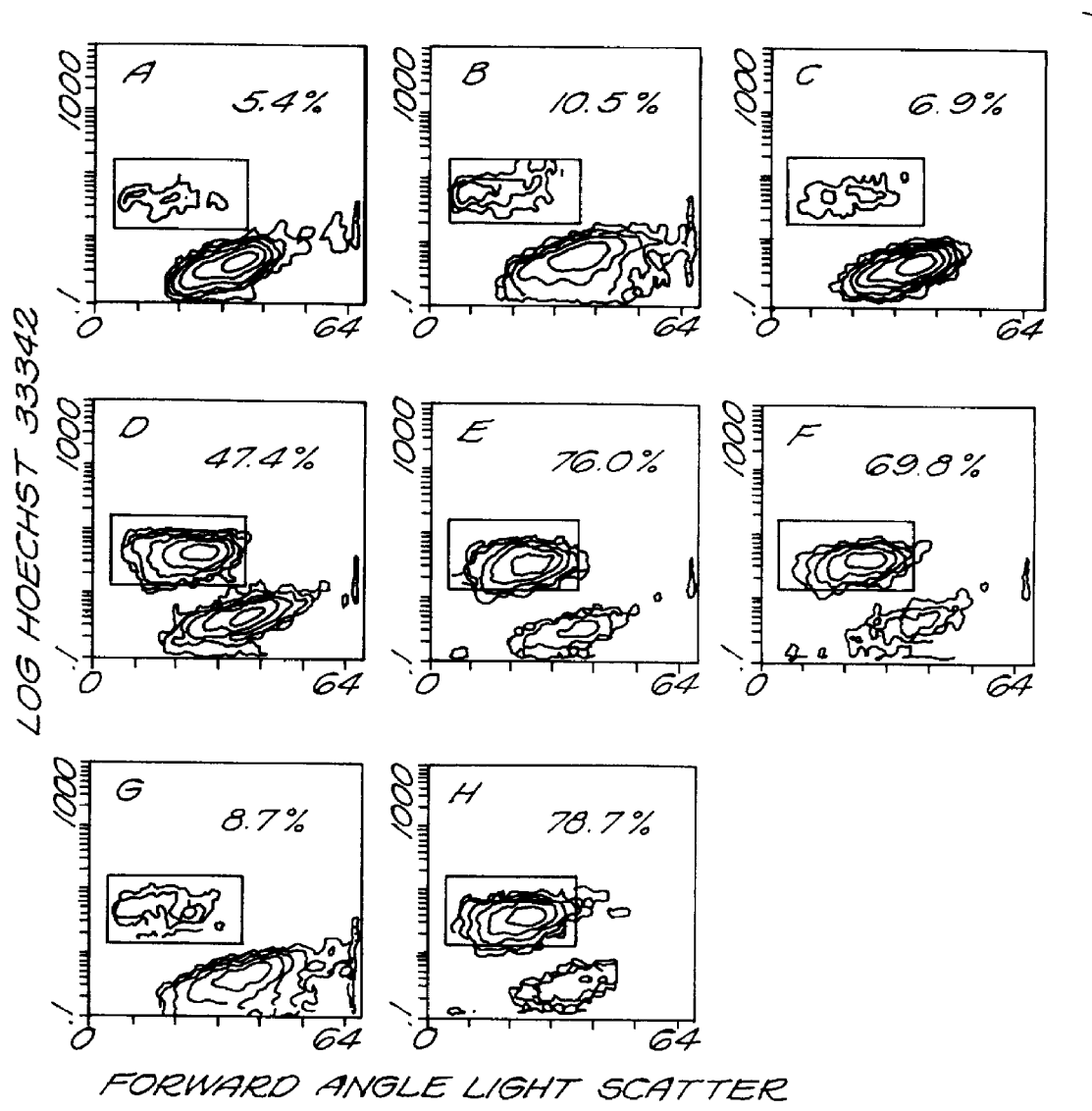
FIG. 1 shows the effect of accessory cells on the induction of apoptosis in PBT cells by PMA.

To define the conditions whereby resting T cells might be induced to undergo apoptosis, a series of preliminary experiments was performed. Our initial studies supported the notion that PBT cells, isolated from normal individuals, are resistant to apoptosis (Kizaki et al., J. Immunol. 143:1790–1794 1989; Wesselborg et al., J. Immunol. 150:4338–4345 1993). It was found, for example, that overnight treatment of purified, freshly-isolated PBT with PMA, ionomycin, dexamethasone, anti-CD95 (Fas/Apo-1) mAb, or mAb crosslinking of cell surface molecules such as CD4, and/or CD3 failed to induce apoptosis. In contrast, a significant degree of apoptosis in the $CD3^+$ population was noted when PBT cells were cultured with autologous, E-rosette$^-$ cells in the presence of PMA. Referring to FIG. 1, the effect of accessory cells on induction of apoptosis in PBT cells by PMA can be seen. PBT cells were incubated for 18 hr in medium alone (FIGS. 1A and 1C) or in PMA-containing medium (10 ng/ml; FIGS. 1B and 1D–H), stained and analysed for apoptotic cells on $CD3^+$ cells by flow cytometry as described in Materials and Methods. The percentages given denote the number of $Ho^{bright}$ and smaller cells within the CD3+ population (Ho: Hoechst 33342 vital dye). In some cases, accessory cells were included in cultures as follows: unfractionated, E-rosette$^-$ cells at 1:2 (FIG. 1D), 1:1 (FIG. 1E), or 5:1 (FIG. 1F) the number of PBT cells; equal numbers of adherent, E-rosette$^-$ cells (FIGS. 1C and 1H); or equal numbers of non-adherent, E-rosette$^-$ cells (FIG. 1G). The final volume of all cultures was 0.5 ml except for FIG. 1F (1.5 ml). The effect of the E$^-$ cells appears to be density dependent since at an E to PBT cell ratio of 1:2 about 50% of the T cells became apoptotic, and this increased to more than 70% when equal numbers of E$^-$ and PBT cells were cultured together. However, no further increase in the percentage of apoptotic T cells was observed when greater numbers of E$^-$ cells were included in the cultures. Indeed, when high numbers of E$^-$ cells were added, larger volumes of media were required to maintain a consistent cell density because it was found that at a high cell density, apoptotic cell death of T cells actually decreased from 70% to 52% due to poor metabolic activity of the cells. Without the addition of E-rosette$^-$ cells, the percentage of PBT cells undergoing apoptosis in PMA-containing medium (FIG. 1B) was only slightly higher than that of PBT cells cultured in medium alone (FIG. 1A). No apoptosis over background levels was observed for T cells cultured in the presence of an equal number of E$^-$ cells when PMA was replaced with ionomycin, dexamethasone, or anti-CD95 (Fas/Apo-1) antibody, or by mAb crosslinking of CD4 and CD3 molecules.

Within the E-rosette$^-$ population, it was found that cells in the adherent population (~90% Mo) induced a strong degree of T cell apoptosis in the presence of PMA (FIG. 1H) yet no apoptosis above background levels was observed when T cells were cultured with nonadherent E$^-$ cells (FIG. 1G). Furthermore, no induction of T cell apoptosis by adherent cells occurred if PMA were not included in the culture medium (FIG. 1C). Consistent with these results, proliferation of PBT in PMA-containing medium, as measured by thymidine incorporation, was 2-fold greater in the presence of 1/10 number of Mo than in the presence of an equal number of Mo.

In addition, an identical degree of T cell apoptosis in PMA-containing medium was found in the presence of either autologous or allogeneic Mo. Moreover, it was demonstrated by using purified T subpopulations that not only $CD4^+$ but also $CD8^-$ T cells undergo apoptosis at a high level (80%) through this Mo-dependent mechanism.

Figure 2A:
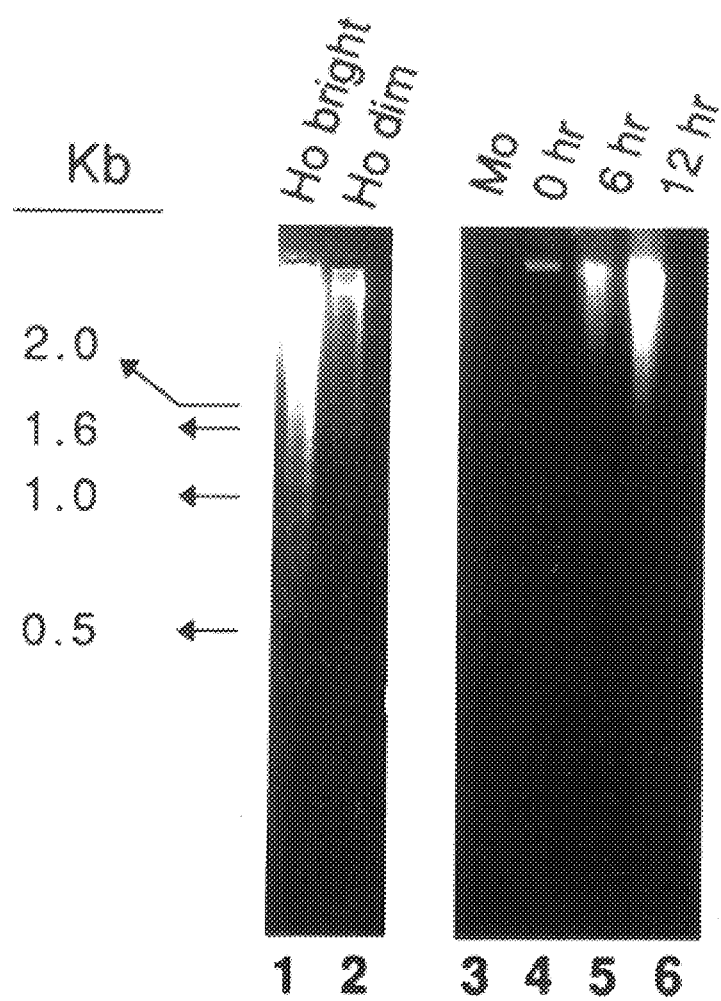
FIGS. 2A and 2B show the measurement of apoptosis by visualization of DNA fragmentation (2A) and fluorescent microscopy of apoptotic cells (2B)
Figure 2B:
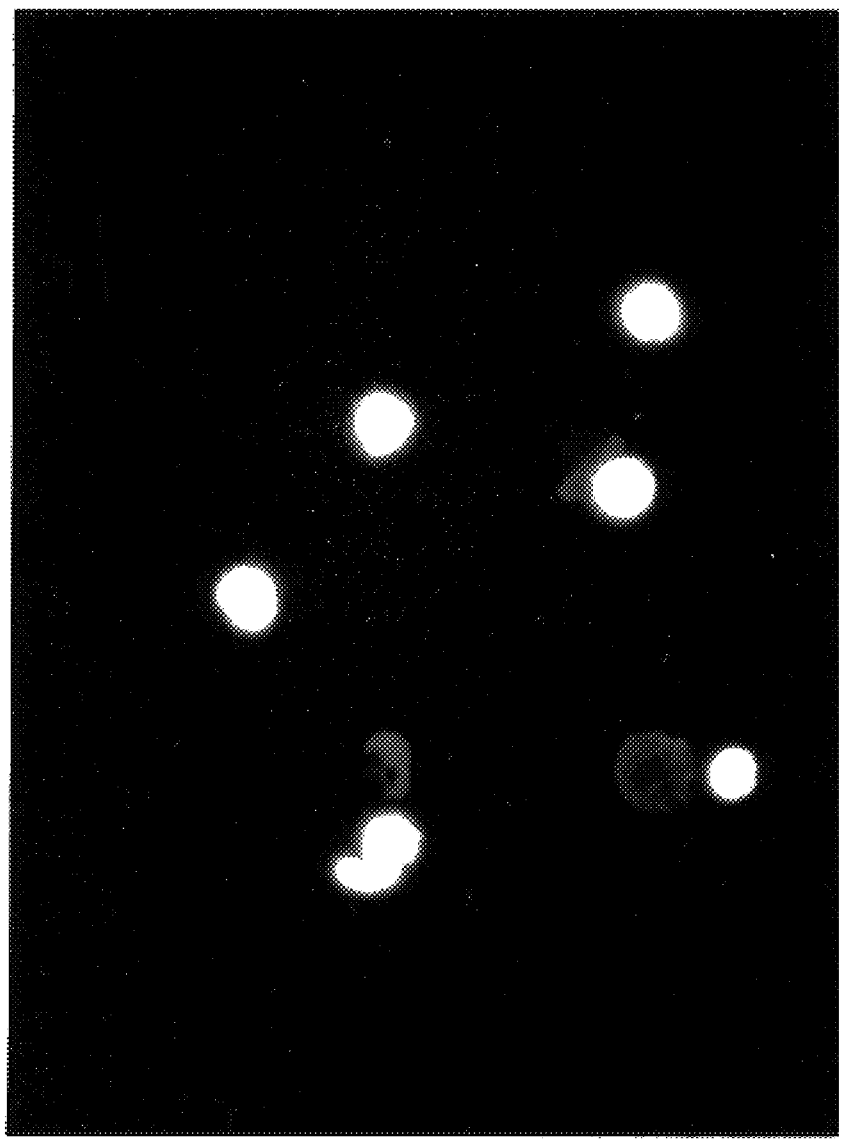

To confirm the apoptotic nature of $Ho^{bright}$ PBT cells, $HO^{bright}$ and $Ho^{dim}$ populations were sorted by flow cytometry and low molecular weight DNA was extracted from an equivalent number of cells ($10^7$) of these two populations. As is shown in FIG. 2A and B, apoptosis can be measured by visualization of DNA fragmentation (FIG. 2A) and fluorescent microscopy of apoptotic cells (FIG. 2B). FIG. 2A: Lanes 1, 2: DNA was extracted from $10^7$ cells of cell sorter purified $Ho^{bright}$ (Lane 1) and $Ho^{dim}$ (Lane 2) populations (as shown in FIG. 1). Lanes 4–6: DNA extracted from PBT cells cultured for the indicated times with an equal number of Mo in PMA medium. Lane 3: DNA extracted from Mo alone treated with PMA for 12 hr. Size of DNA in kb is indicated on the left. FIG. 2B: PBT cells were cocultured with Mo in PMA medium for 16 hr, and collected for staining with Ho and PI. $Ho^{bright}$ cells (a) show condensed nuclei compared with $Ho^{dim}$ cells (b). DNA fragmentation was clearly demonstrated in the $Ho^{bright}$ T cells, but little was seen in the $Ho^{dim}$ T cells (FIG. 2A, lanes 1, 2, respectively). Fluorescence microscopy (FIG. 2B) also showed $Ho^{bright}$ cells (a) had the characteristic condensed nuclei of apoptotic cells compared with normal size nuclei observed in the $Ho^{dim}$ cells (b).

Similar DNA fragmentation analysis was performed on PBT cells cultured with equal numbers of Mo in PMA-containing medium for varying time periods. DNA fragmentation could be seen in the culture containing PBT cells and Mo as early as 6 hr after stimulation with PMA (FIG. 2A, lane 5) and a much greater degree of fragmentation was observed in DNA isolated from cells cultured for 12 hr (FIG. 2A, lane 6). A control 12 hr culture of Mo alone in PMA-containing medium demonstrated that DNA fragmentation as a result of the death of Mo in these cultures was negligible (FIG. 2A, Lane 3).

Contact or Close Proximity between PMA Pretreated Mo and PBT Cells Is Required to Prime PBT for PCD The finding that MHC-mismatched Mo are capable of inducing apoptosis of PBT cells in the presence of PMA raised the possibility that the apoptosis inducing function of Mo may be mediated by soluble factors released into the culture medium after stimulation with PMA. Such soluble factors might then bind to PBT cells resulting in the T cells now becoming susceptible to PMA-induced apoptosis. Two approaches were taken to test such a possibility. First, cell-free culture supernatants were prepared from Mo cultured alone in PMA medium for 1 hr and added to PBT cells. Apoptosis of T cells was then assessed by PI and Ho staining after 18 hr culture, and it was found that no apoptosis was induced by Mo-conditioned medium.

Figure 4:
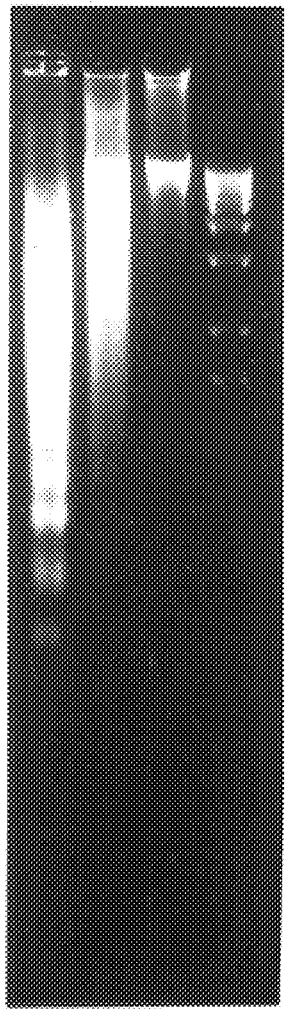
FIG. 4 shows the effect of fixation on the ability of PMA-pretreated Mo to induce apoptosis of PBT cells in PMA medium.

Second, a series of experiments were performed to determine whether contact or close proximity between PBT cells and Mo was required to trigger apoptosis in T cells. In one set of experiments, semipermeable membrane culture inserts were used to separate Mo and PBT cells within the same culture well. As shown in FIG. 3, PBT cells (T) were cultured alone or cocultured with Mo (M) in either the same chamber or the different chambers separated by a semipermeable membrane in the presence of PMA. Results using cells from two different donors and the percentage of apoptotic cells in the T cell population are shown. It was found that when Mo and PBT cells were cultured on the same side of the membrane, in the presence of PMA, a high degree of PBT cell apoptosis was observed. In contrast, when PBT cells and Mo were separated, the percentage of apoptotic cells in the PBT cell population was not significantly greater than that observed with PBT cells cultured alone. In a second set of experiments, Mo were first cultured in PMA medium for 1 hr at 37° C., fixed using 0.5% formaldehyde, then washed extensively and PBT cells were added. Apoptosis of PBT was measured by DNA fragmentation analysis after 18 hr of culture, and the effect of fixation on the ability of PMA-pretreated Mo to induce apoptosis of PBT cells in PMA medium was determined. As shown in FIG. 4, Mo were incubated with PMA (lane 1 and 2) or medium alone (lane 3) for 1 hr at 37° C. and fixed by treatment with 0.5%

(lane 2) or 0.1% (lane 3) formaldehyde; Mo in lane 1 remained unfixed. After washing Mo, PBT cells were cocultured with treated Mo and DNA fragmentation analysis was performed as described in Materials and Methods. 1 kb ladder DNA MW markers are shown in Lane 4. It was found that fixed, PMA-pretreated Mo maintained their ability to sensitize PBT cells for apoptosis (FIG. 4, lane 2). The degree of apoptosis was diminished by approximately 50% compared to that seen using nonfixed, PMA-pretreated Mo (FIG. 4, lane 1). As expected, when Mo were fixed prior to treatment with PMA using an even lower concentration of formaldehyde (0.1%), the fixed Mo were no longer able to prime PBT cells for PMA-induced apoptosis (FIG. 4, lane 3). Together, these results suggest that contact between PBT cells and Mo is required to trigger apoptosis in PMA medium. However, we cannot exclude the possibility that the leakage of soluble ligands into the micro environment of PBT cells from the PMA-pretreated Mo may contribute to the induction of apoptosis.

PMA-Pretreated Mo Enable PBT to Undergo Apoptosis Triggered by Ionomycin, PMA, or Crosslinking of CD3 or CD4

To investigate whether T cells themselves also need to be stimulated in order to initiate the apoptosis process after priming by PMA-treated Mo, Mo were first treated with PMA for 1 hr, washed extensively, and then fixed in 0.1% formaldehyde. To the fixed, PMA-pretreated Mo, fresh PBT cells, some of which had been surface antigen crosslinked using mAb to CD3, CD4, or CD6 plus GAMIg (goat anti-mouse IgG), were added and cultured in either culture medium alone or culture medium containing ionomycin or PMA. In the experiment shown in FIG. 5A, PBT cells were treated with MsIgG (nonimmune mouse IgG) or mAb specific for CD6, CD4, or CD3; bound mAbs were crosslinked with GAMIg (G); and PBT cells were cocultured with 0.1% formaldehyde-fixed Mo for 18 hr. Prior to fixation, the Mo were incubated in either PMA-containing medium (PMA-pretreated Mo) or culture medium (Mo). For ionomycin or PMA stimulation, PBT cells were cultured directly, in the presence of fixed Mo, in culture medium (CM) or in medium containing ionomycin (1 $\mu$g/ml) or PMA (10 ng/ml). In the experiment shown in FIG. 5B, CD4$^+$ cells were treated before culture with rgp120 or with rgp120, anti-rgp120 mAb plus GAMIg and then cocultured with Mo treated as in FIG. 5A. At the end of culture, cells were stained and analysed for the percentage of apoptotic CD3$^+$ cells as described for FIG. 1. As seen in FIG. 5A, after 18 hr, apoptotic cells within the T cell population increased by a factor of almost 2–3 with anti-CD4 and anti-CD3 crosslinking relative to cells which were not treated with mAb in the presence of PMA-treated Mo. Crosslinking of CD6 or prior treatment with control MsIgG caused no increase in the percentage of apoptotic cells. Culturing PBT cells with PMA-treated Mo in medium containing ionomycin or PMA increased the level of apoptosis by almost 3- and 6-fold, respectively. In contrast, when resting PBT cells were cocultured with Mo that were not pretreated with PMA prior to fixation, no significant increase in apoptotic cell death of PBT was observed regardless of the stimuli used, confirming both that Mo have no ability to prime T cells for apoptosis unless treated with PMA prior to fixation and that unprimed PBT cells are resistant to apoptosis. Importantly, the finding suggest that upon culturing with fixed, PMA-pretreated Mo, further stimulation of PBT is required for apoptosis in that no apoptosis was observed for T cells cultured in medium alone or for T cells treated with anti-CD6 mAb plus goat anti-MsIg. Although CD6 is present on virtually all T cells, crosslinking of CD6 with the 6D3 mAb has been shown not to result in T cell activation.

Referring to FIG. 5B, in addition to crosslinking by anti-CD4 mAb, it was found that if CD4 molecules on the cell surface of T cells were crosslinked using a combination of gp120, the envelope glycoprotein of HIV, plus anti-gp120 mAb and GAMIg, apoptosis of primed PBT cells increased by more than 2-fold when compared to unprimed PBT cells. No increase in apoptotic cell death was observed by the binding of gp120 alone without crosslinking.

Materials and Methods

Antibody Reagents. The following monoclonal antibody (mAb) reagents were obtained from Coulter Immunology (Hialeah, FL): FITC-, PE-, or biotin-conjugated mAbs reactive with the lymphocyte surface antigens CD2 (T11-FITC), CD3 (T3-FITC, T3-RD1), CD4 (T4-FITC, T4-Biotin), and CD8 (T8-FITC); MY4-FITC reactive with the monocyte marker CD14; control nonimmune mouse IgG (MsIgG)-FITC and MsIgG-RD1; and purified mAbs specific for CD3 (T3; IgG2). and CD14 (MY4). mAbs against CD4 (19thy 5D7), CD20 (B1), CD8 (21thy2D3), CD56 (N901), and CD6 (6D3) (14, 15) were developed in our laboratory. mAbs against CD16 (3G8) and CD95 (Fas/Apo-1, 7C11) were generous gifts of Drs. P. Anderson and M. J. Robertson (Dana Farber Cancer Institute, Boston, Mass.), respectively. Mouse anti-gp120 (HIV-1) mAb was purchased from INTRACELL Corp. (Cambridge, Mass.). Workshop antibodies are from the Sixth International Conference on Leukocyte Differentiation Antigens.

Purification of PBT Cells and Monocytes. Human PBMC were isolated by Ficoll-Hypaque (Pharmacia Fine Chemicals, Piscataway, N.J.) gradient centrifugation from buffy coats of healthy blood donors, resuspended in culture medium consisting of RPMI 1640, 10% hAB serum, 2 mM L-glutamine, 25 mM HEPES buffer (Sigma Chemical, St Louis, Mo.), 100 IU penicillin/ml and 100 $\mu$g streptomycin/ml (GIBCO, Grand Island, N.Y.), and cultured at 37° C. in tissue culture flasks. After 1 hr incubation, non-adherent cells were collected, washed with Ab reaction buffer [2% hAB serum (Whittaker M. A. Bioproducts, Walkersville, Md.) in RPMI 1640] and then treated with a cocktail of mAbs specific for CD56 (1:250 diluted ascites), CD20 (1:100 diluted ascites), and CD14 (5 $\mu$g/ml) which recognize NK cells, B cells, and Mo, respectively. For CD4$^+$ cell purification, a mAb specific for CD8 (1:200 ascites) was also included in the mAb cocktail. Cells were then purified by negative depletion as previously described (Rasmussen et al., J. Immunol. 152:527–536 1994) and resuspended in culture medium at 10$^6$ cells/ml. Purified PBT cells and CD4$^+$ cells were used in all experiments unless otherwise indicated.

For purification of Mo, E rosette$^-$ cells at 2×10$^6$/ml in culture medium were prepared as described (15) and plated out 5 ml/25 cm$^2$ flask or 0.5 ml to each well of 24 well-plate (Costar, Cambridge, Md.). After 1 hr incubation at 37° C. in 5% CO$_2$, nonadherent cells were removed by washing flasks or plates a total of three times with washing buffer (5% newborn calf serum in RPMI 1640). Remaining adherent cells, consisting of a population of about 90% Mo, as determined by flow cytometry using FITC-anti-CD14 antibody, were used directly as monocytes in apoptosis induction assays.

Flow Cytometric Analysis of Apoptosis. Cells to be analyzed were collected, washed once with FACS medium (2% human AB serum in PBS), and incubated with either FITC-anti-CD2 or FITC-anti-CD3 mAb for 20 min on ice. After a wash cells were resuspended in Hoechst 33342 (Ho) solution (1 $\mu$g/ml in RPMI 1640), incubated for 12 min at 37° C., and then immediately placed on ice. Propidium iodide (PI) was added to each sample to give a final concentration of 1 μg/ml (both Ho and PI purchased from Sigma) before flow cytometric analysis. Quantification of apoptotic cell death in the CD3$^+$ population was performed by flow cytometric analysis using an Epics Elite (Coulter Electronics) (Scmid et al., Cytometry 15:12–20 1994). Cell debris and clumps were excluded from analysis by using forward and side scatter parameters. All fluorescent signals were recorded as logarithmic scale and analyzed using Epics Elite software.

Apoptosis Induction. Mo were incubated in either culture medium alone or PMA in culture medium (10 ng/ml) for 1 hr at 37° C., then washed 3 times. In some experiments, formaldehyde (0.1–1% in RPMI-1640) was added to fix the cells for 15 min at room temperature before washing. To wells containing either treated or untreated Mo, purified PBT cells were added (0.5 ml at 10$^6$ cells/ml) and cocultures were incubated for 16–18 hr at 37° C. in the presence or absence of various stimuli as indicated. PBT cells were then analyzed for apoptosis as described for the particular experiment.

In some cases, PBT cell surface antigens were crosslinked using saturating concentrations of specific mAbs plus goat anti-mouse IgG (GAMIg) where indicated (Rasmussen et al., J. Immunol. 152:527–536 1994) prior to culture. Crosslinking CD4 molecules via recombinant HIV-1 gp120 was carried out on purified CD4$^+$ cells which were first incubated with gp120 (American Bio-Technologies, Cambridge, Mass.) at 2.5 μg per 10$^6$ cells in 100 μl Ab reaction buffer for 40 min at room temperature, washed once with Ab reaction buffer, and then incubated with anti-gp120 mAb (10 μg/ml) for 20 min on ice. Cells were washed again and treated with GAMIg as above before coculturing with Mo.

DNA Fragmentation. PBT cells (10$^7$/10 ml) were cultured in 25 cm$^2$ flasks containing Mo which had been previously treated as indicated; PMA was included in cultures where noted. After overnight culture at 37° C., the cells were washed once in PBS and then pelleted by centrifugation in Eppendorf tubes. DNA Extraction and Electrophoresis were done as described (Cohen et al., J. Immunol. 132:38–42 1984).

Staining of Apoptotic Cells and Fluorescence Microscopy. Cells to be examined microscopically were pelleted in Eppendorf tubes by centrifugation for 10 seconds at 13,000 rpm. The cell pellet was resuspended, stained with 10 μl of Ho solution containing 1 μg/ml PI, placed on ice and immediately examined under a Zeiss ICM fluorescence microscope with UV excitation and blue emission. Blue fluorescence was. visualized when the sample was warmed up during the time of examination. Photographs were taken with either Kodak Tri-X or TMAX 400 film.

Production of Monoclonal Antibodies Capable of Blocking Monocyte-Mediated T Cell Apoptosis. BALB/c mice were immunized by intraperitoneal injection of 2×10$^7$ PMA-treated monocytes in a 100 nl volume per mouse mixed with an equal volume of complete Freund's adjuvant (Sigma). Three additional intraperitoneal injections were given at 2–3 week intervals using the same amount of antigen mixed with incomplete Freund's adjuvant. The final immunization was administered by injection of antigen alone without adjuvant into the tail vein of the mouse. Three days later, the mouse was sacrificed by cervical dislocation. Spleen cells were isolated from the immunized mouse spleen and fused with NS-1 myeloma cells by the method described in Wayne M. Yokoyama, Current Protocols in Immunology, P 2.5.1–2.5.17, 1991). When clones were visible by eye (about 2 weeks), hybridoma supernatants were screened for reactivity to fixed, PMA-treated monocytes by a conventional ELISA assay using anti-mouse IgG (H&L) alkaline phosphatase conjugate (Promego #S372B) and Alkaline Phosphatase Substrate Kit (Bio-Rad, 172–1064). Monocytes stimulated by lipopolysaccharides (LPS) were screened in parallel since LPS-stimulated monocytes appeared to adhere to the well surface as well as PMA-treated monocytes but had no effect on T cell viability. Hybridomas showing higher reactivity to PMA-treated monocytes than to LPS-treated monocytes were further tested for the ability to block monocyte-mediated T cell apoptosis by detection of viable cells remained in the wells after apoptosis induction as described below.

Blocking Monocyte-Mediated T Cell Apoptosis with Antibodies. Monocytes were prepared from PBMC as described above and plated out to 96 well-plates (Costar, Cambridge, Mass.) at approximately 1×10$^5$ monocytes adherent on the well surface. Hybridoma supernatants or diluted ascites with known antigen specificities of 100 nl were added into each well of the plate. After 15 min at room temperature, purified PBT cells 0.1 ml/well at 1×10$^6$ cells/ml in culture medium containing 15 ng/ml PMA were added and the plates were incubated for 40 hr at 37° C. with 50% CO$_2$. To test viable cells remaining in each well, cellTiter 96 AQneous non-radioactive kit from Promego (G5421, Madison, Wis.) was used according to instructions. In brief, 100 nl of culture medium was carefully removed; then 20 nl/well of combined MTS/PMS solution was added. After 1–2 hr at 37° C. with 5% CO$_2$, absorbance of 492 nm was recorded using an ELISA plate reader (Titertek Multiskan MCC/340). Abs that can increase the absorbance value to two times that of control samples (without addition of mAbs) are considered as positive inhibitors of Mo-dependent T cell apoptosis.

Method for Identifying and Cloning a Differentially Expressed Gene in Mo after PMA Treatment. mRNA populations are isolated from Mo and PMA treated Mo, and then cDNA is produced with reverse transcription beginning at oligo-dT primer, followed by amplification of cDNA via PCR reaction employing oligo-dT and arbitrary in sequence at 3' as primers. The amplified cDNA subpopulations of both cells as defined by each primer pair are distributed on a DNA sequencing gel side by side. The cDNA pieces specific for PMA-treated Mo will be cloned and sequenced to identify some of the genes through GeneBank. Further cloning to obtain a complete gene of interest will be carried out by screening the cDNA library with the cDNA fragment as a probe. The cloned genes will be transfected into THP-1 cells, a human monocyte cell line lacking the ability to prime T cells for apoptosis after PMA treatment, in order to test for their ability to sensitize T cells to apoptotic cell death.

USE

Our data show that freshly isolated, normally resistant PBT cells can be readily primed to undergo apoptosis by stimulation via crosslinking of CD3 or CD4 molecules, ionomycin or PMA through a MHC-nonrestricted Mo-dependent mechanism. Infection with macrophage-trophic strains of HIV-1 and HIV-2 should similarly activate macrophages to prime CD4$^+$ and CD8$^+$ T cells for apoptosis. Therefore, it will be possible to mitigate the severe immunodeficiency associated with AIDS by interfering with the association between HIV-infected antigen presenting cells, especially monocytes and macrophages, and T cells.

It has been proposed that T cell apoptosis is a key in AIDS development. However, up until the discoveries reported here, how T cells in HIV infected individuals are primed for apoptosis was entirely unknown. Indeed, HIV-infected chimpanzees show no increase in the degree of apoptotic T cell death (Gougeon et al., AIDS Research & Human Retroviruses 9:553–563 1993). These HIV-infected chimpanzees neither develop AIDS-like disease nor have significantly immunodefective T cell function, even though they are persistently infected with T cell-tropic HIV variants. Interestingly, HIV does not infect Mo in chimpanzees in contrast to human HIV infection, where Mo-tropic HIV variants can be isolated in all the stages of HIV infection (Schuitemaker et al., J. Infect. Dis., 168:1190–1197 1993). In support of the view that Mo play a crucial role in maintaining T cell number in HIV infected individuals is the observation that macrophage-tropic HIV strains but not T cell-tropic HIV strains cause extensive $CD4^+$ cell depletion in the hu-PBL-SCID model despite equivalent virus burden (Mosier et al., Science 260:689–692 1993). Banda et al. have suggested that crosslinking of CD4 molecules with a combination of gp120 and anti-gp120 Ab can prime T cells for apoptosis since crosslinking of bound gp120 on human $CD4^+$ cells followed by engagement of TcR results in apoptosis in vitro (Banda et al., J. Exp. Med. 176:1099–1106 1992). This, however, cannot explain the death of $CD8^+$ T cells from $HIV^+$ individuals upon in vitro culture. Our demonstration that both $CD4^+$ and $CD8^+$ T cells can be primed for apoptosis by PMA-treated Mo and that the primed T cells can now undergo apoptosis upon activation suggests a model whereby infection of macrophages with a macrophage-tropic HIV results in activation of these cells, either by direct infection or secondarily to cytokines released as a result of infection (Mosier et al., Immunol. Today 15:332–339 1994). The activated macrophages would then be envisioned to facilitate induction of apoptosis on susceptible PBT cells in a manner similar to that described for PMA treated-Mo. This mechanism, applicable to other virus infections as well, might be employed in lymphoid tissues where a high ratio of infected macrophages to T cells can be found (Embretson et al., Nature 362:359–362 1993). These T cells would be particularly susceptible to apoptosis upon further stimulation as might occur following antigen recognition, superantigen binding, CD4 molecule crosslinking by membrane associated gp160 on the infected macrophages, and/or CD4 crosslinked by gp120 in the presence of anti-gp120 Ab. Such a process could result in the continuous and slow depletion of $CD4^+$ cells and even of those activated $CD8^+$ cells which are primed to kill virus infected targets. This model should hold true not only in HIV but also in Epstein-Barr virus (EBV), cytomegalovirus (CMV) and LCMV as these viruses are also not T cell-trophic (EBV infects primarily B lymphocytes, whereas in LCMV and CMV, macrophages are primarily infected), but can still induce T cells to undergo apoptosis (Uehara et al., Blood 80: p 452 1992; Meyaard et al., J. Clin. Invest. 93: 982, 1994; Razvi et al., J. Virol. 67:5754, 1993).

One possible candidate for the cell surface molecule or ligand on Mo that is important in priming T cells for apoptosis is the membrane-bound form of TNF-α, which is expressed by Mo upon PMA stimulation (31). However, neither anti-rTNF-αmAb nor anti-rTNF-α receptor p60 and p80 mAbs, either alone or in combination, were able to block Mo-dependent apoptosis of PBT cells triggered by PMA.

It is unclear at this point if CD95 (Fas/Apo-1) molecule is involved in the observed Mo-mediated apoptosis of PBT cells. What is unlikely, however, is that the process is mediated solely through CD95 molecule since no enhancement in the number of apoptotic T cells was detected when freshly isolated PBT cells were stimulated with either a combination of PMA and anti-CD95 (Fas/Apo1) antibody, 7C11, or anti-CD95 alone for 18 hr at 37° C.

Although a monocyte-specific apoptotic ligand has not yet been isolated, we do know that it is expressed on monocytes that are primed with PMA, but not on unstimulated monocytes, or on B cells. Furthermore, we have developed a polyconal anti-serum against activated monocytes that can block the priming of apoptosis in an in vitro assay. In addition, we have tested almost 600 different Workshop antibodies from the Sixth International Conference on Leukocyte Differentiation Antigens and found that mAbs against the following molecules can partially block Mo-dependent T cell apoptosis: CD45, CD45RA, CD11c, CD11b, CD11a, CD18, CD95, CD63 like, CD100. The involved ligand(s) will be identified using standard immunological techniques and any novel ligand(s) will be cloned as described above. Once the ligand has been cloned and its nucleotide sequence determined, it may be possible to regulate expression of the ligand by interfering with transcription or translation of the gene, for example using anti-sense technology.

Assays for screening. candidate inhibitors can readily be developed using well known techniques for detecting the characteristic morphological changes in the dying cell, such as the DNA fragmentation detection system described in Materials and Methods. Other techniques that could be used involve propidium iodide staining and FACS analysis and direct visualization using visible light and electron microscopy. Candidate inhibitors can also be tested using cells from asymptomatic HIV carriers or the SCID hu mouse model described earlier.

Preferred inhibitors include antibodies that bind to an epitope present on an PAC apoptotic ligand, e.g., a polyclonal anti-serum or one or more of the Workshop antibodies, as described above. Therapeutic compositions containing agents capable of interfering with the association between lentivirus-infected antigen presenting cells and T lymphocytes may be administered to an affected individual orally, topically, or parenterally, (e.g., intranasally, subcutaneously, intramuscularly, intravenously, or intraarterially) by routine methods in pharmaceutically acceptable inert carrier substances. Optimal dosage and modes of administration can readily be determined by conventional protocols.

Although the invention has been shown and described with respect to illustrative embodiments thereof, it should be appreciated that the foregoing and various other changes, omissions and additions in the form and detail thereof may be made without departing from the spirit and scope of the invention as delineated in the following claims.

We claim:

1. A method of screening for an inhibitor of antigen presenting cell-mediated priming of resting peripheral blood T lymphocytes to undergo activation induced apoptosis, said method comprising the steps of:

providing first and second samples of components for a T lymphocyte apoptosis assay, said components comprising resting peripheral blood T lymphocytes and stimulated antigen presenting cells selected from the group consisting of monocytes, macrophages and dendritic cells, said stimulated antigen presenting cells being provided for priming said T lymphocytes to undergo apoptosis;

causing said first sample of components to react in said apoptosis assay, wherein the extent of T lymphocyte apoptosis in said first assay sample is determined;

adding a candidate inhibitor to said second sample of components;

causing said second sample of components containing said candidate inhibitor to react in said apoptosis assay, wherein the extent of T lymphocyte apoptosis in said second assay sample is determined; and comparing said extent of T lymphocyte apoptosis in said first assay sample to said extent of T lymphocyte apoptosis in said second assay sample to determine the effect of said candidate inhibitor.

2. The method of claim 1 wherein said apoptosis assay is an in vitro assay.

3. The method of claim 1 wherein said apoptosis assay is an in vivo assay.

4. The method of claim 1 wherein said stimulated antigen presenting cells are monocytes or macrophages.

5. The method of claim 1 wherein said antigen presenting cells are stimulated with phorbol myristate acetate or phytohaemagglutinin.

6. The method of claim 1 wherein said antigen presenting cells are infected with a macrophage-tropic strain of HIV.

7. The method of claim 1, wherein said resting peripheral blood T lymphocytes and said stimulated antigen presenting cells are present in a ratio of about 2:1 in each of said sample of components for a T lymphocyte apoptosis assay.

8. The method of claim 1, wherein said resting peripheral blood T lymphocytes and said stimulated antigen presenting cells are present in a ratio of about 1:1 in each of said sample of components for a T lymphocyte apoptosis assay.

* * * * *

UNITED STATES PATENT AND TRADEMARK OFFICE
CERTIFICATE OF CORRECTION

PATENT NO : 5,843,635
DATED : December 1, 1998
INVENTOR(S): Stuart F. Schlossman, et al.

It is certified that error appears in the above-identified patent and that said Letters Patent is hereby corrected as shown below:

Title page, item 75] Inventors: "Mei X. Wu" should read --Meixiong Wu--.

Column 5, line 58, "$CD8^-$" should read --$CD8^+$--.

Column 9, line 50, "was.visualized" should read --was visualized--.

Column 11, line 59, "anti-rTNF-αmAb" should read --anti-rTNF-α mAb--.

Signed and Sealed this

Sixteenth Day of November, 1999

Attest:

Q. TODD DICKINSON

Attesting Officer

Acting Commissioner of Patents and Trademarks